United States Patent
Kawakubo

(10) Patent No.: US 8,231,385 B2
(45) Date of Patent: Jul. 31, 2012

(54) DENTAL HANDPIECE WITH PRESSURE REGULATING MECHANISM

(75) Inventor: Kiyoshi Kawakubo, Kanuma (JP)

(73) Assignee: Nakanishi Inc., Kanuma-shi (JP)

( * ) Notice: Subject to any disclaimer, the term of this patent is extended or adjusted under 35 U.S.C. 154(b) by 0 days.

(21) Appl. No.: 12/774,036

(22) Filed: May 5, 2010

(65) Prior Publication Data

US 2010/0209871 A1    Aug. 19, 2010

Related U.S. Application Data

(63) Continuation of application No. 11/450,432, filed on Jun. 12, 2006, now abandoned.

(30) Foreign Application Priority Data

Jun. 16, 2005    (JP) .................................. 2005-176549

(51) Int. Cl.
*A61C 5/14*    (2006.01)

(52) U.S. Cl. ....................................................... 433/137

(58) Field of Classification Search .................. 433/132, 433/128, 133, 131; 137/115.13, 116.3, 115.26; 166/311, 323, 321, 316; 415/904; 606/80
See application file for complete search history.

(56) References Cited

U.S. PATENT DOCUMENTS

| | | | |
|---|---|---|---|
| 4,257,484 A | 3/1981 | Whitley et al. | |
| 4,744,752 A | 5/1988 | Nakayama et al. | |
| 4,791,950 A | 12/1988 | Pedersen | |
| 4,944,349 A | 7/1990 | Von Gonten, Jr. | |
| 5,372,197 A | 12/1994 | Wacker | |
| 6,065,966 A | 5/2000 | Loehn et al. | |
| 6,827,096 B1 | 12/2004 | Kayukawa | |

FOREIGN PATENT DOCUMENTS

| | | |
|---|---|---|
| JP | 2003-19144 | 1/2003 |
| JP | 2004-351086 A | 12/2004 |

OTHER PUBLICATIONS

Fluid. (n. d.). Dictionary.com Unabridged. Retrieved May 25, 2011, from Dictionary.com website: http://dictionary.reference.com/browse/fluid.*

* cited by examiner

*Primary Examiner* — Heidi M Eide
(74) *Attorney, Agent, or Firm* — Jason D. Voight

(57) ABSTRACT

The present dental handpiece has a burr sleeve, a head section, an air supply passage for introducing compressed air into the head section for driving the burr sleeve, and an air discharge passage for discharging the compressed air. The air supply passage includes a through hole axially extending through the rear terminal part of the handpiece, and a tubular pressure regulating member and an air supply tube connected in series between the through hole and the head section. The pressure regulating member has an aperture for allowing communication with the air discharge passage, and an annular valve body arranged axially slidably for opening/closing the aperture. When the pressure of compressed air passing through the air supply passage exceeds a predetermined level, the valve body is slid to open the aperture to discharge the compressed air for regulating the pressure of the compressed air to be supplied to the burr sleeve.

9 Claims, 6 Drawing Sheets

DENTAL HANDPIECE WITH PRESSURE REGULATING MECHANISM

This is a continuation of application Ser. No. 11/450,432, which has been abandoned, filed Jun. 12, 2006, the entire specification of which is hereby incorporated by reference herein.

FIELD OF ART

The present invention relates to a dental handpiece, in particular to a dental handpiece wherein the pressure of compressed air passing through an air supply passage is down-regulated when the pressure exceeds a predetermined level.

BACKGROUND ART

Dental handpieces that are rotatably driven by compressed air are conventionally known, such as those having an air turbine or an air motor. An example of such a conventional dental handpiece is shown in FIG. 5.

FIG. 5 is a sectional view of head section 40 of an air-turbine dental handpiece. This dental handpiece includes burr sleeve 42 for receiving and detachably holding dental treatment tool 41 therein, rotor 43 provided on the burr sleeve 42 for rotatably driving the burr sleeve 42 with compressed air, and upper and lower ball bearings 44 provided above and below the rotor 43 for rotatably supporting the burr sleeve 42. These parts are all accommodated in cartridge case 45, which is in turn housed in head housing 46. Head housing jacket 47 supporting the head housing 46 contains therein air supply passage 48a for supplying compressed air to the rotor 43 and air discharge passage 48b for discharging the compressed air supplied to the rotor 43.

The air-turbine dental handpiece discussed above has drawbacks in that, if the handpiece is operated at an air pressure that exceeds the acceptable level predetermined for each handpiece, the revolution speed of the turbine becomes too high, and the dental treatment tool may be damaged. Further, the lubricant may run out prematurely to cause wearing of the bearings, which disadvantageously reduces their service life.

In order to avoid these drawbacks, a dental unit which supplies compressed air to the handpiece is given functions to regulate the pressure of the compressed air to be supplied to the handpiece, so as to keep the air pressure in the air supply passage in the handpiece within the predetermined range. However, the pressure of the compressed air needs to be adjusted properly for each kind of dental handpiece, and such pressure adjustment requires complex operations. Thus the user may tend to use the same air pressure for different kinds of handpieces, and as a result, the above problems will occur.

In order to solve the above problems, the assignee of the present application has proposed in JP-2003-019144-A a dental handpiece having a pressure reducing member. This dental handpiece has a pressure reducing member arranged in the handpiece body section, or in the coupling (connector section) to be connected to the rear end of the handpiece body section. FIG. 6 illustrates dental handpiece 50 as the former embodiment.

The dental handpiece 50 includes grip section 51 and head section 52 provided at the distal end of the grip section 51. The head section 52 houses and rotatably supports a burr sleeve (not shown) for receiving dental treatment tool 53 therein. The grip section 51 accommodates air supply tube 54, air discharge passage 55, and water supply line 56, and pressure reducing member 60 is disposed in the intermediate part of the air supply tube 54. A flexible tube (not shown) extending from a dental unit for supplying compressed air is connected to the rear end of the grip section 51, so that the compressed air is supplied through the air supply tube 54 to the head section 52 to rotatably drive the dental treatment tool 53.

In the dental handpiece 50 discussed above, when the pressure of the compressed air supplied from the dental unit exceeds the acceptable level, the air pressure is automatically regulated by discharging the compressed air out of the air supply tube 54 through the pressure reducing member 60 into the air discharge passage 55.

The dental handpiece 50 disclosed in JP-2003-019144-A is advantageous in that the air pressure is automatically regulated. However, since the pressure reducing member 60 is disposed projecting in the intermediate part of the air supply tube 54, the grip section 51 inevitably becomes thicker, which poses problems in grippability.

In addition to the embodiment shown in FIG. 6, JP-2003-019144-A also discloses a dental handpiece having the pressure reducing member provided in the coupling. However, for providing the pressure reducing member in the coupling, relatively complex material processing is required during the production process, and thus further improvement is required.

Besides the handpieces disclosed in JP-2003-019144-A, there are other conventional dental handpieces that have a pressure reducing section integrally incorporated in the rear terminal part of the dental handpiece body. However, the above problems, such as the difficulties in making the grip section compact, and relative complexity in production process, still remain in these dental handpieces.

SUMMARY OF THE INVENTION

The present invention aims to solve the above problems in view of the drawbacks in the prior art. It is an object of the present invention to provide a dental handpiece which is capable of automatically regulating the pressure of the compressed air supplied from a dental unit, when it exceeds an acceptable level, to prevent the revolution speed of the dental treatment tool from becoming too high; which requires less complexity in material processing in its production process; and which is easy for medical practitioners to grip.

In order to solve the above problems, according to the present invention, there is provided a dental handpiece comprising:

a burr sleeve for receiving a dental treatment tool therein, a head section housing and rotatably supporting said burr sleeve therein, an air supply passage for introducing compressed air into the head section for rotatably driving the burr sleeve with the compressed air, and an air discharge passage for discharging the compressed air, wherein said air supply passage comprises:

a through hole axially extending through a rear terminal part of the dental handpiece, and a tubular pressure regulating member and an air supply tube connected in series between the distal end of the through hole and the head section, said tubular pressure regulating member having an aperture in its intermediate part for allowing communication with the air discharge passage, and an annular valve body arranged axially slidably for selectively opening and closing said aperture, wherein, when a pressure of compressed air passing through the air supply passage exceeds a predetermined level, said annular valve body is slid to open the aperture, whereby the compressed air is discharged through the aperture into the air discharge passage for regulating the pressure of the compressed air to be supplied to the burr sleeve.

According to the dental handpiece of the present invention, since pressure regulation of the compressed air to be supplied to the head section is performed by means of a tubular pressure regulating member, and this tubular pressure regulating member is formed as a separate part from the rear terminal part of the dental handpiece, neither the coupling (connecting section) or the rear terminal part of the dental handpiece has to undergo complex material processing, which is required in conventional dental handpieces, and thus the production cost may be reduced.

In addition, the tubular pressure regulating member is connected in series with the rear terminal part and with the air supply tube to form itself a part of the air supply passage through the dental handpiece. Its tubular form allows compact arrangement of this member in the dental handpiece. Further, the tubular pressure regulating member has an outlet aperture for the compressed air in the intermediate part of its tubular body, and the valve body for opening/closing the outlet aperture is formed in an annular shape and arranged coaxially in the tubular body. Thus the tubular pressure regulating member may be made thin, and thus the grip section of the dental handpiece may be made relatively thin.

In a preferred embodiment of the dental handpiece according to the present invention, the tubular pressure regulating member further comprises:

a first tubular member, a second tubular member inserted in said first tubular member to form a gap therebetween, and a spring for biasing said annular valve body, wherein said aperture of the tubular pressure regulating member is provided in each of said first and second tubular members at a predetermined position for allowing communication between the interior of the tubular pressure regulating member and the air discharge passage, wherein the annular valve body and the spring are arranged in the gap between said first and second tubular members, wherein said annular valve body is biased by the spring into a position to prevent communication between the apertures in the first and second tubular members, and is arranged to receive pressure from the compressed air passing through the air supply passage, wherein, when the pressure of the compressed air passing through the air supply passage exceeds a predetermined level, the annular valve body is slid by the pressure against the force of the spring to provide communication between the apertures.

Since the dental handpiece according to the present invention is provided with a tubular pressure regulating member, the pressure of the compressed air received from a dental unit may automatically be adjusted properly when it exceeds the acceptable level, so that the revolution speed of the dental treatment tool will not become too high. Further, since the tubular pressure regulating member is connected in series with the rear terminal part and with the air supply tube, the overall dental handpiece may be made compact for allowing easy gripping by medical practitioners.

PREFERRED EMBODIMENTS OF THE INVENTION

The present invention will now be explained in more detail with reference to preferred embodiments taken in conjunction with the attached drawings, which are illustrative only and do not intend to limit the present invention.

Figure 1:
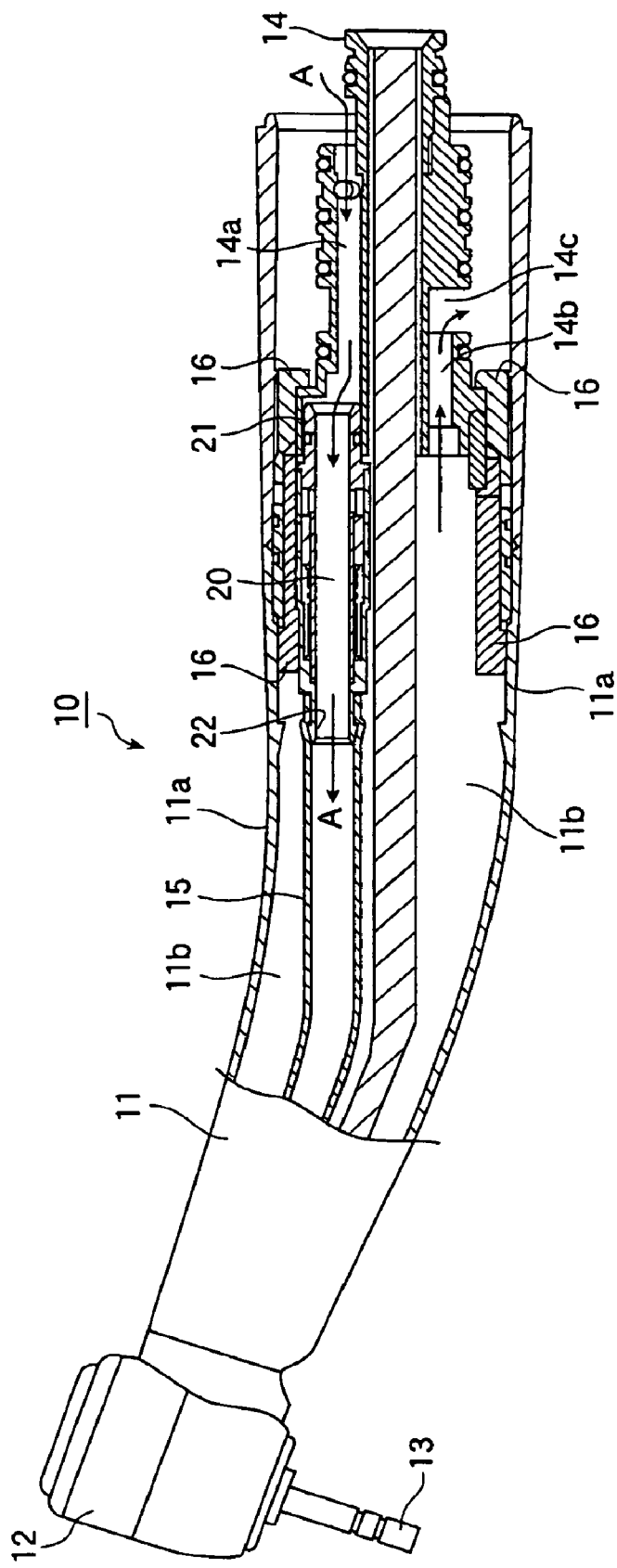
FIG. 1 is a side view, partially in section, of the dental handpiece according to the present invention.

FIG. 1 shows dental handpiece 10 according to the present invention in a side view, partially in section.

The dental handpiece 10 of the present invention includes grip section 11 having casing 11a. At the distal end of the grip section 11 is provided head section 12, which houses and rotatably supports a burr sleeve (not shown) for receiving dental treatment tool 13 therein. In the proximal end of the grip section 11 is formed rear terminal part 14 for detachably connecting to a coupling (not shown) as a connector section. The grip section 11 also has air supply tube 15 therein, and pressure regulating member 20 is connected between the air supply tube 15 and the rear terminal part 14. The coupling (not shown) to be connected to the rear terminal part 14 is in turn connected to a dental unit (not shown) via a flexible tube (not shown) extending from the rear end of the coupling to the dental unit, so that compressed air is supplied from the dental unit through the rear terminal part 14 to the head section 12 to rotatably drive the burr sleeve.

The rear terminal part 14 is fixed in the casing 11a of the grip section 11 by means of fixing member 16. The rear terminal part 14 has air inlet 14a in the form of a through hole for allowing passage of the compressed air supplied through the coupling, and air outlet 14b and air outlet groove 14c for discharging the compressed air into the coupling. The casing 11a has hollow 11b inside, which functions as an air discharge passage for guiding the air discharged from the head section 12 back through the air outlet 14b and the air outlet groove 14c.

The pressure regulating member 20 is connected to the air inlet 14a at its proximal end 21, and to the air supply tube 15 at its distal end 22, so that the pressure regulating member 20 is connected in series with the distal end of the rear terminal part 14 and with the air supply tube 15 along a generally common axis. Compressed air taken in through the rear terminal part 14 passes through the pressure regulating member 20 in the direction of arrow A, and then through the air supply tube 15 to the head section 12.

Figure 2:
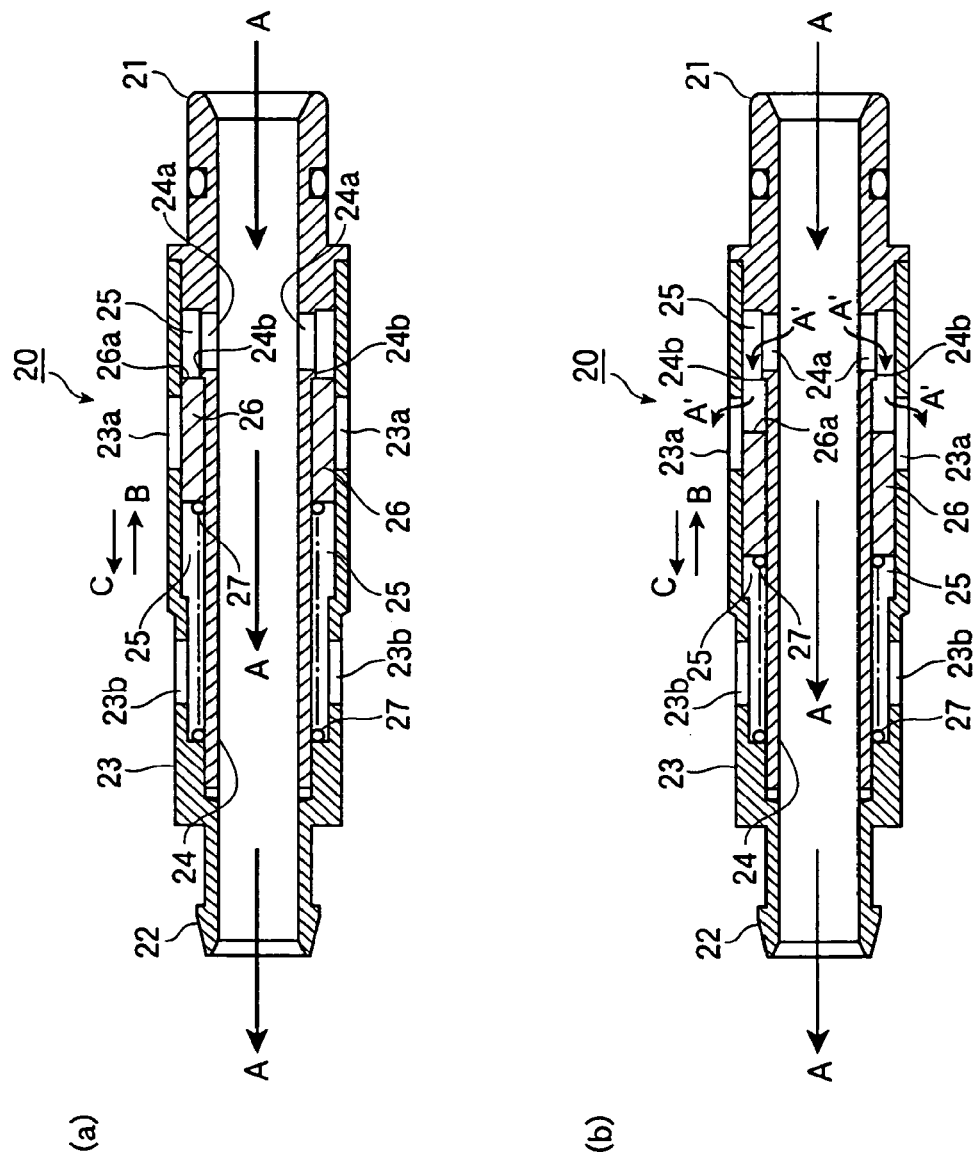
FIGS. 2(a) and 2(b) are sectional views of the tubular pressure regulating member used in the present invention.

Referring to FIGS. 2(a) and 2(b), the pressure regulating member 20 includes first tubular member 23, second tubular member 24 inserted partially into the first tubular member 23 to form gap 25 therebetween, and an annular valve element 26 slidably disposed in the gap 25. The valve element 26 is biased in the direction of arrow B by means of spring 27 also disposed in the gap 25. The first and second tubular members 23 and 24 have apertures 23a and 24a, respectively, penetrating the members and arranged alternately. The apertures 23a and 24a are arranged such that, when the annular valve element 26 is in the position as shown in FIG. 2(a) under the biasing force of the spring 27, the apertures 23*a* and 24*a* are not in communication with each other and are thus closed, whereas when the annular valve element 26 is in the position as shown in FIG. 2(*b*), the apertures 23*a* and 24*a* are in communication with each other via the gap 25 and are thus opened. Air vent aperture 23*b* is provided through the first tubular member 23 for opening the gap 25 to allow sliding motion of the annular valve element 26. The second tubular member 24 has flange 24*b* protruding near the aperture 24*a*. The annular valve element 26 biased by the spring 27 engages with this flange 24*b* and is stopped at the position shown in FIG. 2(*a*). When the annular valve element 26 is in the position as shown in FIG. 2(*a*), the rear surface 26*a* of the annular valve element 26 receives the pressure from the compressed air through the aperture 24*a* and the gap 25.

As discussed above, since the pressure regulating member 20 is formed as a separate member from the rear terminal part 14 of the dental handpiece body, the rear terminal part 14 does not have to undergo complex material processing as in the conventional handpiece. This may contribute to reduction in production costs. Since the pressure regulating member 20 is in a tubular form, and is connected in series with the rear terminal part 14 and with the air supply tube 15 to form itself a part of the air supply passage through the dental handpiece, the pressure regulating member 20 may be accommodated in the dental handpiece in a compact manner. Further, the pressure regulating member 20 may be formed by inserting the second tubular member 24 into the first tubular member 23 and arranging the annular valve element 26 in the gap 25 between the first and second tubular members 23 and 24, and the apertures 23*a* and 24*a* are selectively opened and closed simply by the sliding motion of the annular valve element 26 in the gap 25. Thus the pressure regulating member 20 may be formed with a reduced thickness, which allows to relatively reduce the thickness of the grip section 11 of the dental handpiece.

Incidentally, the rear terminal part 14, the pressure regulating member 20, and the air supply tube 15 may be connected in series in a manner different from the embodiment shown in FIG. 1.

Figure 3:
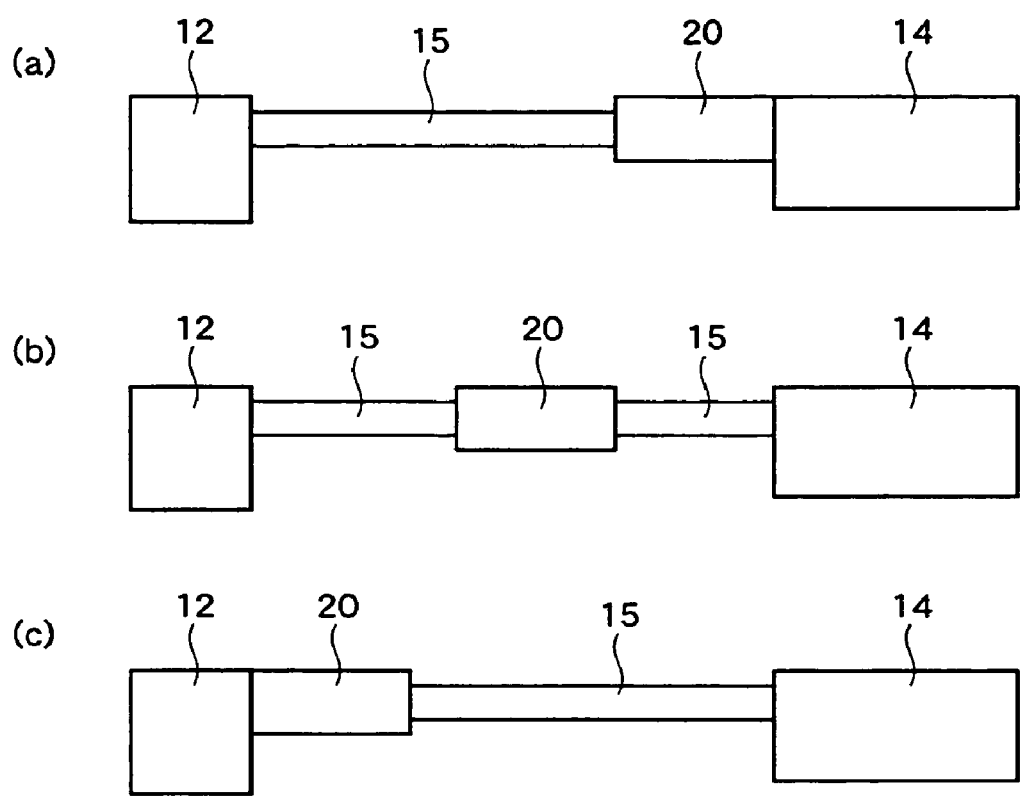
FIGS. 3(a) to 3(c) schematically illustrate the series arrangement of the rear terminal part, the pressure regulating member, and the air supply tube in the handpiece body.

That is, in the dental handpiece 10 illustrated in FIG. 1, as shown schematically in FIG. 3(*a*), the pressure regulating member 20 is connected at one end thereof directly to the rear terminal part 14, and at the other end thereof, with the head section 12 by the air supply tube 15, to form the series arrangement. Alternatively, as shown in FIG. 3(*b*), the pressure regulating member 20 may be connected at one end thereof with the rear terminal part 14 by the air supply tube 15, and at the other end thereof with the head section 12 by the air supply tube 15, or as shown in FIG. 3(*c*), the pressure regulating member 20 may be connected at one end thereof with the rear terminal part 14 by the air supply tube 15, and at the other end thereof directly to the head section 12.

Next, the function of the dental handpiece 10 is explained with reference to FIGS. 1 and 2.

The compressed air fed from the dental unit is received via the coupling through the air inlet 14*a* of the rear terminal part 14, passed through the pressure regulating member 20 and the air supply tube 15, and supplied to the head section 12 to rotatably drive the burr sleeve (not shown) having the dental treatment tool 13 received therein. On the other hand, the compressed air discharged from the head section 12 is passed through the hollow 11*b* of the dental handpiece 10, through the air outlet 14*b* and air outlet groove 14*c*, and is discharged outside via the coupling or the like.

Here, when the pressure of the compressed air through the air inlet 14*a*, the pressure regulating member 20, and the air supply tube 15 is within the tolerance level, the annular valve element 26 biased by the spring 27 engages with the flange 24*b* to stay at the position shown in FIG. 2(*a*), whereby all the compressed air is allowed to pass through the pressure regulating member 20.

On the other hand, when the pressure of the compressed air through the air inlet 14*a*, the pressure regulating member 20, and the air supply tube 15 exceeds the tolerance level, that is, when the compressed air entering through the aperture 24*a* of the second tubular member 24 and the gap 25 applies pressure on the rear surface 26*a* of the annular valve element 26 that exceeds the biasing force of the spring 27, the annular valve element 26 is slid to the direction of arrow C. This causes the aperture 24*a* of the second tubular member 24 to communicate with the aperture 23*a* of the first tubular member 23 via the gap 25, i.e., the apertures 24*a* and 23*a* to open, as shown in FIG. 2(*b*), to allow the compressed air to be discharged out of the pressure regulating member 20 into the hollow 11*b* as shown by arrows A'. In this way, when the pressure of the compressed air exceeds the predetermined level, the pressure regulating member 20 discharges the compressed air into the hollow 11*b*, so that the pressure of the compressed air in the air supply tube 15 downstream of the pressure regulating member 20 is maintained constantly within the predetermined range. This allows automatic regulation of the revolution speed of the dental treatment tool 13 within the predetermined level.

Figure 4:
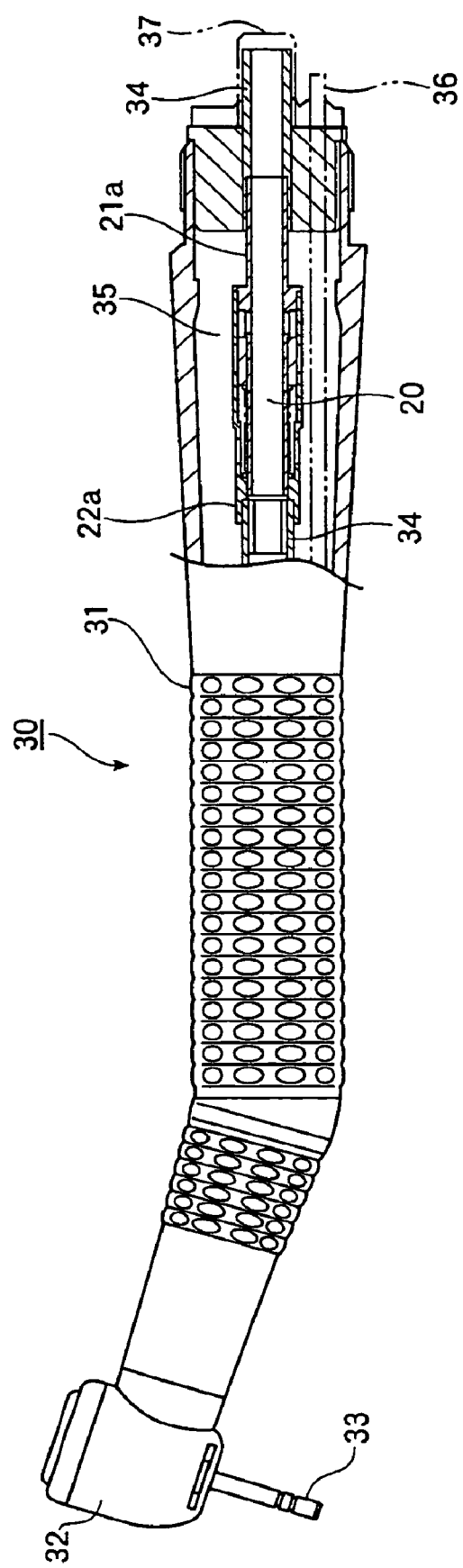
FIG. 4 is a side view showing the pressure regulating member of FIG. 2 applied to a dental handpiece of a type different from that of FIG. 1.
Figure 5:
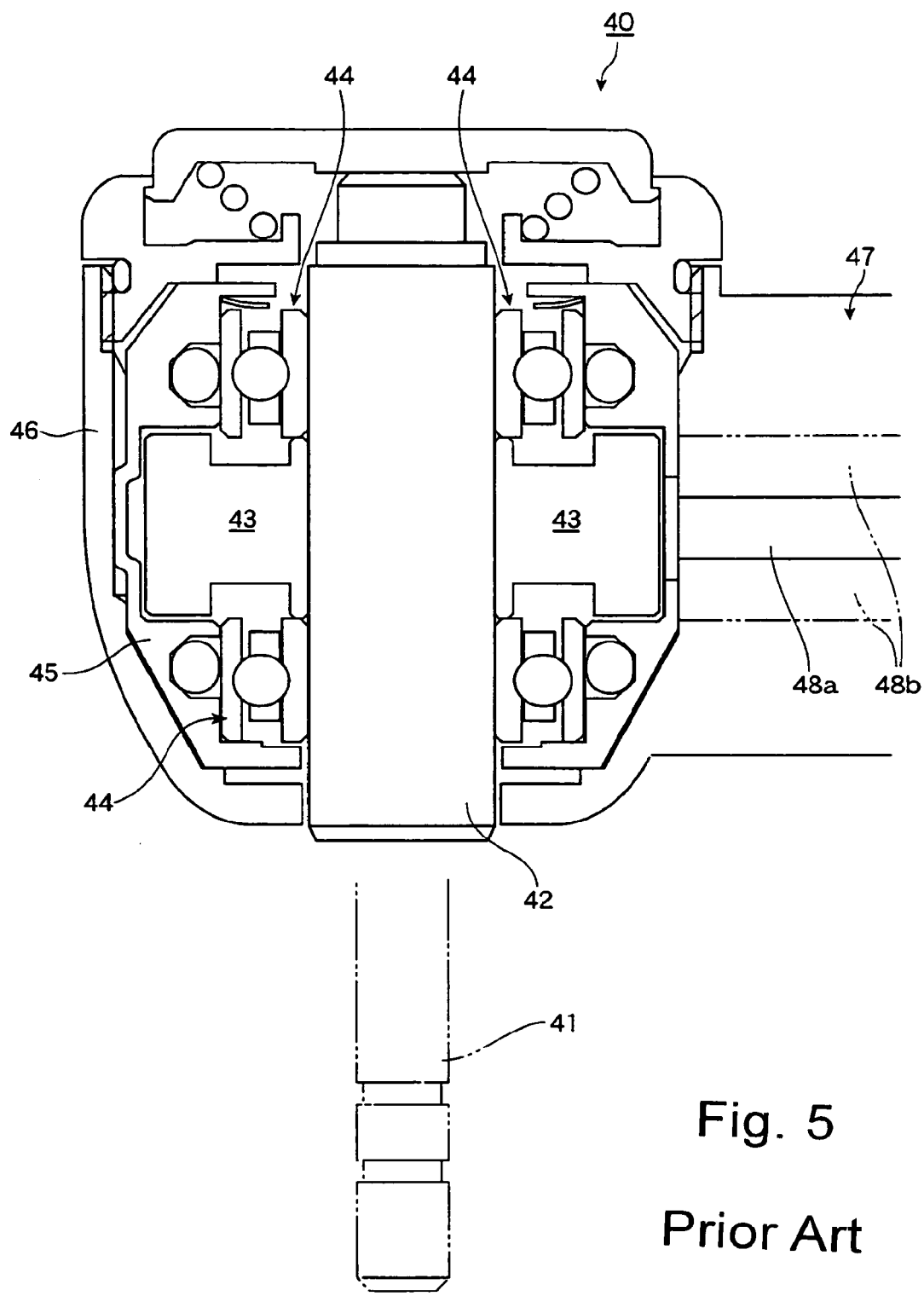
FIG. 5 is a sectional view of the head section of a conventional dental handpiece.
Figure 6:
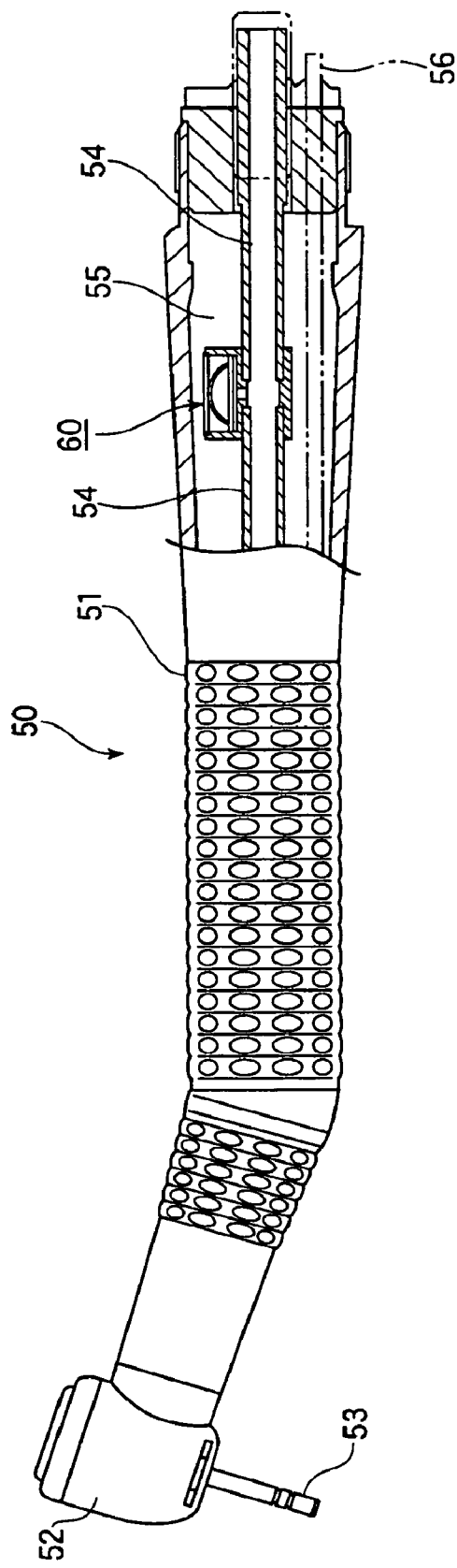
FIG. 6 is a sectional view, partially in section, of a conventional dental handpiece having a pressure regulating mechanism.

Another embodiment is explained with reference to FIG. 4. FIG. 4 is a side view, partially in section, of dental handpiece 30, wherein the pressure regulating member 20 of FIG. 2 is applied to a dental handpiece of a different type. The dental handpiece 30 includes grip section 31 and head section 32 provided at the distal end of the grip section 31. The head section 32 houses and rotatably supports a burr sleeve (not shown) for receiving dental treatment tool 33 therein. The grip section 31 accommodates air supply tube 34, air discharge passage 35, and water supply line 36, with the air supply tube 34 and the water supply line 36 extending beyond the rear end of the dental handpiece 30. Air discharge tube 37 is attached to the rear end of the dental handpiece 30. The pressure regulating member 20 is disposed in the intermediate part of the air supply tube 34, and a flexible tube (not shown) extending from an apparatus such as a dental unit (not shown) for supplying compressed air is connected to the rear end of the grip section 31, so that the compressed air is supplied through the air supply tube 34 to the head section 32 to rotatably drive the dental treatment tool 33.

Incidentally, the pressure regulating member 20 of FIG. 2 is slightly modified for adapting to the embodiment of FIG. 4 in that its proximal and distal ends 21*a* and 22*a* are formed to be connectable to the air supply tube 34 of FIG. 4, while the other structure and function of the member 20 remain the same in both embodiments.

Although the present invention has been described with reference to the preferred embodiment, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:
1. A dental handpiece comprising:
    a burr sleeve for receiving a dental treatment tool therein,
    a head section housing rotatably supporting said burr sleeve therein, an air supply passage for introducing compressed air into the head section housing for rotatably driving the burr sleeve with the compressed air, and an air discharge passage for discharging the compressed air, wherein said air supply passage comprises:

a through hole axially extending through a rear terminal part of the dental handpiece, and a tubular pressure regulating member and an air supply tube connected in series between a distal end of the through hole and the head section housing, said tubular pressure regulating member further comprising:

a first tubular member, a second tubular member inserted in said first tubular member to form a gap therebetween, an aperture provided in each of said first and second tubular members at a predetermined position for allowing communication between an interior of the tubular pressure regulating member and the air discharge passage, an annular valve body arranged axially slidably for selectively allowing and preventing communication between said apertures, and a spring for biasing said annular valve body, wherein the aperture in the second tubular member is axially displaced from the aperture in the first tubular member, wherein the annular valve body and the spring are arranged in the gap between said first and second tubular members, wherein the annular valve body fits between said first and second tubular members slidably and contacts both said first and second tubular members, wherein said annular valve body is biased by the spring into a position to prevent communication between the apertures in the first and second tubular members, and is arranged to receive pressure from the compressed air passing through the air supply passage, wherein, when a pressure of compressed air passing through the air supply passage exceeds a predetermined level, said annular valve body is slid by the pressure against the force of the spring to provide communication between the apertures, whereby the compressed air is discharged through the apertures into the air discharge passage for regulating the pressure of the compressed air to be supplied to the burr sleeve.

2. The dental handpiece according to claim 1, wherein the tubular pressure regulating member is connected at one end thereof directly to the through hole, and at the other end thereof with the head section housing by the air supply tube.

3. The dental handpiece according to claim 1, wherein the tubular pressure regulating member is connected at one end thereof with the through hole by the air supply tube, and at the other end thereof with the head section housing by the air supply tube.

4. The dental handpiece according to claim 1, wherein the tubular pressure regulating member is connected at one end thereof with the rear terminal part by the air supply tube, and at the other end thereof directly to the head section housing.

5. The dental handpiece according to claim 1, wherein said annular valve body receives pressure from the compressed air on its rear surface to slide to open the aperture of the first tubular member.

6. The dental handpiece according to claim 1, wherein the apertures in the first and second tubular members are arranged alternately.

7. The dental handpiece according to claim 1, wherein an air vent aperture is provided through said first tubular member for opening the gap.

8. The dental handpiece according to claim 1, wherein said second tubular member has a flange protruding downstream of its aperture, and said annular valve body biased by the spring engages with said flange to stop at said position with the aperture in the second tubular member opened to the gap and with the aperture in the first tubular member closed to the gap.

9. The dental handpiece according to claim 1, wherein said second tubular member has been partially inserted in said first tubular member, and wherein one end of the tubular pressure regulating member is formed with one end of one of the first and second tubular members, and the other end of the tubular pressure regulating member is formed with one end of the other of the first and second tubular members.

* * * * *